United States Patent [19]
Paetz et al.

[11] Patent Number: 5,741,936
[45] Date of Patent: Apr. 21, 1998

[54] PROCESS FOR THE PREPARATION OF 3-CHLORO-3'-NITRO-4'-METHOXYBENZOPHENONE

[75] Inventors: Klaus-Christian Paetz, Burscheid-Hilgen; Helmut Fiege, Leverkusen; Wolfram Kissener, Neunkirchen-Seelscheid, all of Germany

[73] Assignee: Bayer Aktiengesellschaft, Leverkusen, Germany

[21] Appl. No.: 710,474

[22] Filed: Sep. 18, 1996

[30] Foreign Application Priority Data

Sep. 25, 1995 [DE] Germany ............ 195 35 500.8

[51] Int. Cl.$^6$ .................................................. C07C 45/61
[52] U.S. Cl. .................................................. 568/306
[58] Field of Search .................................................. 568/306

[56] References Cited

U.S. PATENT DOCUMENTS

| | | | |
|---|---|---|---|
| 4,288,620 | 9/1981 | Rosner | 564/144 |
| 4,339,618 | 7/1982 | Rosner | 564/144 |
| 4,361,704 | 11/1982 | Onopchenko et al. | 568/306 |
| 4,560,800 | 12/1985 | Bakshi et al. | 568/306 |

FOREIGN PATENT DOCUMENTS

| | | | |
|---|---|---|---|
| 0023557 | 2/1981 | European Pat. Off. | 568/306 |
| 0260744 | 3/1988 | European Pat. Off. | 568/307 |
| 198039 | 10/1989 | Hungary | 508/307 |

OTHER PUBLICATIONS

Chemical Abstracts, vol. 107, No. 25, Dec. 21, 1987, Columbus, Ohio, US; Abstract No. 236236k, Seite 741; Spalte 2; XP002022340 *Zusammenfassung* & RO 91 633 A (Intreprinderea de Medicamente "Terapia").

A.H.M. Raeymaekers, Synthesis and Anthelminthic Activity of Alkyl–(5–acyl–1–H–benzimidazol–2–yl) Carbamates, Arzneim.–Forsch./Drug Res., 28 (1), Heft 4, pp. 586–594, (1978).

*Primary Examiner*—James H. Reamer
*Attorney, Agent, or Firm*—Sprung Kramer Schaefer & Briscoe

[57] ABSTRACT

3-Chloro-3'-nitro-4'-methoxybenzophenone with substantially lower contents of dinitro derivatives than hitherto is obtained if 3-chloro-4'-methoxybenzophenone is nitrated in from 65 to 85% strength by weight sulfuric acid with nitric acid at temperatures in the range from −20° to +60° C.

8 Claims, No Drawings

PROCESS FOR THE PREPARATION OF 3-CHLORO-3'-NITRO-4'-METHOXYBENZOPHENONE

The present invention relates to a process for the preparation of 3-chloro-3'-nitro-4'-methoxybenzophenone with a very low content of dinitro derivatives in the crude product.

3-Chloro-3'-nitro-4'-methoxybenzophenone is an intermediate which can be used for the preparation of pharmaceutical active principles (see e.g. EP-A 260 744).

It is known to prepare 3-chloro-3'-nitro-4'-methoxybenzophenone by nitrating 3-chloro-4'-methoxybenzophenone in methylene chloride as solvent using a mixed acid, or carrying out the nitration in glacial acetic acid/acetic anhydride as solvent using 65% strength by weight nitric acid at 15° C. (see Arzneimittel-Forschung 28/4, pp. 586–594 (1978)).

A disadvantage of these processes is that the crude 3-chloro-3'-nitro-4'-methoxybenzophenone is obtained with a content of 3–6% by weight of dinitro derivatives. These dinitro derivatives are a disruption in the course of subsequent reaction to form pharmaceutical active principles and must therefore be removed. Using customary purification methods, for example recrystallization from a solvent, however, it is virtually impossible to remove these impurities if their content in the crude product is more than 4% by weight. Even lower contents of dinitro derivatives in the crude product require purification measures, which are associated with high losses of substance and are therefore uneconomic.

In the subsequent course of the synthesis of pharmaceutical active principles it is also not possible to separate off, in a satisfactory manner, dinitro derivatives or their follow-on products.

The object is therefore to find a process for the preparation of 3-chloro-3'-nitro-4'-methoxybenzophenone, in which process dinitro derivatives are formed in a markedly smaller amount than hitherto.

A process has now been found for the preparation of 3-chloro-3'-nitro-4'-methoxybenzophenone by nitrating 3-chloro-4'-methoxybenzophenone, which process comprises carrying out nitration in 65–85% strength by weight sulfuric acid as reaction medium with nitric acid at temperatures in the range from −20° to +60° C.

It is important to keep within this sulfuric acid concentration range in order to obtain a good-quality product. The contents of dinitro derivatives in products prepared in this way are generally less than 0.5% by weight. In the process according to the invention it is preferred to employ 70–80% strength by weight sulfuric acid.

The amount of sulfuric acid used as a reaction medium for the nitration can be varied within wide limits. It is preferably such as to give, at the beginning of the reaction, an essentially homogeneous reaction mixture and to provide for stirrability of the reaction mixture present at the end of the nitration reaction. For example, it is possible to use 500–2500 g of sulfuric acid per 100 g of 3-chloro-4'-methoxybenzophenone employed. This amount is preferably 1000–1800 g.

The concentration of the nitric acid which is to be employed as reactant in the process according to the invention can be, for example, in the range 50–100% by weight. Preference is given to 50–70% strength by weight nitric acid, and especially the product with a strength of about 63% by weight which is commercially available as concentrated nitric acid. The nitric acid can be employed as it is or in any desired mixtures with sulfuric acid. If such nitric/sulfuric acid mixtures are employed they can comprise, for example, from 30 to 60% by weight sulfuric acid (calculated as 100% strength by weight acid, present as from 96 to 100% strength by weight acid) and from 40 to 70% by weight of nitric acid of the concentration indicated above.

In principle, the amount of nitric acid for the process according to the invention can be varied within wide ranges. Preference is given to 80–150% by weight of the stoichiometrically required amount. A smaller amount of nitric acid leads to incomplete conversions and is therefore uneconomic, while an increase in the amount of nitric acid above 150% by weight of the stoichiometrically required amount does not promote the selectivity of the reaction and therefore makes little sense from an economic standpoint. In the process according to the invention, particular preference is given to employing an amount of nitric acid which corresponds to 90–120% by weight of the stoichiometrically required amount.

The reaction temperature in the process according to the invention is from −20° to +60° C. A lower limit is placed on the reaction temperature by the slowdown in the nitration reaction and by the poor solubility of 3-chloro-4'-methoxybenzophenone in the sulfuric acid at this level. Temperatures of more than 60° C. lead frequently to a decline in the selectivity. Temperatures in the range from 0° to +40° C. are preferred.

The reaction mixture which is present after the end of the nitration reaction and, optionally, following the conclusion of an after-stirring period can be worked up, for example, by filtering off the precipitate formed, washing the filter cake, for example with water, and finally drying it. The crude product obtainable in this way contains less than 0.5% by weight of dinitro derivatives. If desired the crude product can be purified further, for example by reprecipitation from an appropriate solvent. The crude product is generally obtained in purities of 93% or more. The pure product can be isolated in yields of 85% of theory or more and with purities of more than 95% by weight. Examples of suitable solvents for reprecipitation are isopropanol, diisopropyl ether and toluene.

EXAMPLES

The examples which follow are intended to illustrate the process according to the invention without restricting it to the particularities described therein. The starting product employed was 3-chloro-4'-methoxybenzophenone, which had been prepared in a known manner by Friedel-Crafts reaction from m-chlorobenzoyl chloride and anisole.

Example 1

175 ml of 80% strength by weight sulfuric acid were initially introduced into a stirred apparatus, and 22.2 g of 3-chloro-4'-methoxybenzophenone were dissolved therein at room temperature. The resulting solution was clear and yellow. The mixture was then cooled to +10° C., and 10.5 g of 65% strength by weight nitric acid were metered in over the course of 1 hour. During the metered addition, the crude nitro compound precipitated from the reaction solution. After the end of metered addition, stirring was continued at +10° C. for 1 hour and then the yellow solid was filtered off on a sintered-glass suction filter. The crystals were washed with water and dried to give 24.6 g of crude product with a purity of 96% by weight. The crude product contained 1.5% by weight of the starting material and had a content of dinitro derivatives of less than 0.5% by weight. The reprecipitation of this crude product from 250 ml of isopropanol gave 23 g of a product with a purity of more than 99% by weight. This corresponds to a yield of 88% of theory. The melting point of the purified product was 113° C.

Example 2

The procedure of Example 1 was repeated but carrying out the nitration in 175 ml of 75% strength by weight sulfuric acid at +20° C. and employing 11.5 g of 65% strength by weight nitric acid. Following the isolation by filtration, washing and drying, a crude product with a purity of 94% by weight was obtained which contained 3.5% by weight of unreacted starting material and less than 0.4% by weight of dinitro derivatives. This crude product was purified in the same manner as that described in Example 1 to give a product with a purity of more than 99% by weight.

Example 3 (For Comparison)

22 ml of 65% strength by weight nitric acid were run over the course of 15 minutes into a mixture of 43.3 g of 3-chloro-4'-methoxybenzophenone, 700 ml of dichloromethane and 44 ml of concentrated sulfuric acid at from +10° to +15° C. After the end of the addition, the mixture was subsequently stirred at 10° C. for 1 hour. Following the addition of water to the crude nitration solution, the organic phase was separated off, dried with sodium bicarbonate and concentrated on a rotary evaporator, to leave 50 g of a crude product which contained 93.9% by weight of 3-chloro-3'-nitro-4'-methoxybenzophenone, 3.0% by weight of dinitro derivatives, 0.3% by weight of unreacted starting product, with the remainder to 100% being constituted by unknown substances. The yield of crude product was 92% of theory.

What is claimed is:

1. A process for the preparation of 3-chloro-3'-nitro-4'-methoxybenzophenone by nitrating 3-chloro-4'-methoxybenzophenone, which comprises carrying out the nitration in from 65 to 85% strength by weight sulfuric acid as reaction medium, without organic solvents, with 50–100% wt. concentration nitric acid at temperatures in the range from −20° to +60° C.

2. The process as claimed in claim 1, wherein from 70 to 80% strength by weight sulfuric acid is employed.

3. The process as claimed in claim 1, wherein from 500 to 2500 g of sulfuric acid are employed, based on 100 g of 3-chloro-4'-methoxybenzophenone.

4. The process as claimed in claim 1, wherein nitric acid with a concentration in the range from 50 to 100% by weight is employed in an amount which corresponds to from 80 to 150% by weight of the stoichiometrically required amount.

5. The process as claimed in claim 1, wherein the nitration is carried out at from 0° to +40° C.

6. The process as claimed in claim 1, wherein the reaction mixture present at the end of the nitration reaction is worked up by filtering off the precipitate formed, washing the filter cake and drying it.

7. The process as claimed in claim 1, wherein the reaction mixture present at the end of the nitration reaction and after the conclusion of an afterstirring period is worked up by filtering off the precipitate formed, washing the filter cake and drying it.

8. The process as claimed in claim 1, wherein the crude product obtained by filtering off the precipitate formed, washing the filter cake and drying it is purified further by reprecipitation from an appropriate solvent.

* * * * *